United States Patent
Kalkbrenner (10) Patent No.: US 10,119,914 B2
(45) Date of Patent: Nov. 6, 2018

(54) FAST HIGH-RESOLUTION MICROSCOPY METHOD AND FAST HIGH-RESOLUTION MICROSCOPE

(71) Applicant: Carl Zeiss Microscopy GmbH, Jena (DE)

(72) Inventor: Thomas Kalkbrenner, Jena (DE)

(73) Assignee: CARL ZEISS MICROSCOPY GMBH, Jena (DE)

( * ) Notice: Subject to any disclaimer, the term of this patent is extended or adjusted under 35 U.S.C. 154(b) by 148 days.

(21) Appl. No.: 15/380,880

(22) Filed: Dec. 15, 2016

(65) Prior Publication Data

US 2017/0176337 A1 Jun. 22, 2017

(30) Foreign Application Priority Data

Dec. 16, 2015 (DE) .................. 10 2015 121 920

(51) Int. Cl.
*G02B 21/16* (2006.01)
*G01N 21/64* (2006.01)
(Continued)

(52) U.S. Cl.
CPC ..... *G01N 21/6458* (2013.01); *G02B 21/0004* (2013.01); *G02B 21/16* (2013.01); *G02B 21/367* (2013.01)

(58) Field of Classification Search
CPC .. G01N 21/6458; G02B 21/16; G02B 21/367; G02B 21/0004
See application file for complete search history.

(56) References Cited

U.S. PATENT DOCUMENTS

| 8,084,754 B2 | 12/2011 | Hell et al. |
| 2004/0212799 A1 | 10/2004 | Hell |

(Continued)

FOREIGN PATENT DOCUMENTS

| DE | 103 25 460 A1 | 11/2004 |
| DE | 10 2006 021 317 B3 | 10/2007 |

(Continued)

OTHER PUBLICATIONS

Bates, Mark, et al., "Multicolor Super-Resolution Imaging with Photo-Switchable Fluorescent Probes," *Science*, vol. 317, pp. 1749-1753 (Sep. 21, 2007).

(Continued)

*Primary Examiner* — David Porta
*Assistant Examiner* — Faye Boosalis
(74) *Attorney, Agent, or Firm* — Christensen, Fonder, Dardi & Herbert PLLC (57) ABSTRACT

A fast, high-resolution localization microscopy method for a specimen containing fluorescence emitters. In a bright state, emitters emit fluorescent radiation upon excitation irradiation, and in a dark state, the fluorescence emitters do not emit fluorescent radiation upon excitation irradiation. The emitters can be brought from the bright state into the dark state by irradiation, and the dark state has a lifetime after which the emitters return to the bright state spontaneously, such that the emitters blink at a blinking frequency. The blinking specimen is imaged with a spatial resolution and detected with a camera, the intensity of the radiation is set such that emitters are isolated in the individual images in terms of the spatial resolution, and the refresh rate at which the images are produced is not lower than the blinking frequency. Locations are determined for isolated emitters in the images with an accuracy that exceeds the spatial resolution.

25 Claims, 4 Drawing Sheets

(51) Int. Cl.
G02B 21/00 (2006.01)
G02B 21/36 (2006.01)

(56) References Cited

U.S. PATENT DOCUMENTS

| | | | |
|---|---|---|---|
| 2008/0032414 | A1 | 2/2008 | Zhuang et al. |
| 2009/0237501 | A1 | 9/2009 | Lemmer et al. |
| 2011/0025831 | A1 | 2/2011 | Bewersdorf et al. |
| 2011/0081653 | A1 | 4/2011 | Hell et al. |
| 2012/0014317 | A1 | 1/2012 | Rahman |
| 2012/0224034 | A1 | 9/2012 | Kalkbrenner et al. |
| 2012/0313012 | A1 | 12/2012 | Selvin et al. |
| 2013/0155218 | A1 | 6/2013 | Kalkbrenner et al. |
| 2013/0256563 | A1 | 10/2013 | Kalkbrenner et al. |
| 2014/0184777 | A1 | 7/2014 | Kleppe et al. |
| 2014/0198198 | A1 | 7/2014 | Geissbuehler et al. |
| 2014/0287941 | A1 | 9/2014 | Betzig et al. |
| 2015/0015879 | A1* | 1/2015 | Papadopoulos ........ G02B 23/26 356/301 |
| 2016/0195704 | A1 | 7/2016 | Kalkbrenner et al. |

FOREIGN PATENT DOCUMENTS

| | | |
|---|---|---|
| DE | 10 2008 024 568 A1 | 12/2009 |
| DE | 21 2009 000 043 U1 | 2/2011 |
| DE | 10 2012 205 032 A1 | 10/2013 |
| DE | 10 2013 216 124 A1 | 2/2015 |
| WO | WO 2006/127692 A2 | 11/2006 |
| WO | WO 2016/049544 A1 | 3/2016 |

OTHER PUBLICATIONS

Betzig, Eric, et al., "Imaging Intracellular Fluorescent Proteins at Nanometer Resolution," *Science*, vol. 313, pp. 1642-1643 (Sep. 15, 2006).
Betzig, Eric, et al., "Supporting Online Material for: Imaging Intracellular Fluorescent Proteins at Nanometer Resolution," *Science Express*, 31 pgs. (Aug. 10, 2006).
Booth, M. J., et al., "Low-cost, frequency-domain, fluorescence lifetime confocal microscopy," *Journal of Microscopy*, vol. 214, Pt. 1, pp. 36-42 (Apr. 1, 2004).
Chao, Jerry, et al., "Ultrahigh accuracy imaging modality for super-localization microscopy," *Nature Methods*, 8 pgs. (Mar. 3, 2013).
Fölling, Jonas, et al., "Fluorescence nanoscopy by ground-state depletion and single-molecule return," *Nature Methods*, vol. 5, No. 11, pp. 943-945 (Nov. 2008).
Gunkel, Manuel, et al., "Dual color localization microscopy of cellular nanostructures," *Biotechnol. J.*, vol. 4, pp. 927-938 (2009).
Heilemann, Mike, et al., "Carbocyanine Dyes as Efficient Reversible Single-Molecule Optical Switch," *J. Am. Chem. Soc.*, vol. 127, pp. 3801-3806 (2005).
Heilemann, Mike, et al., "Subdiffraction-Resolution Fluorescene Imaging with Convention fluorescent Probes," *Angew. Chem. Int. Ed.*, vol. 47, pp. 6172-6176 (2008).
Heilemann, Mike, et al., "Super-resolution imaging with small organic Fluorophores," *Angew. Chem. Int. Ed.*, vol. 48, 12 pgs. (2009).
Hell, S.W., et al., "Ground-state-depletion fluorescence microscopy: a concept for breaking the diffraction resolution limit," *Applied Physics B., Lasers and Optics*, vol. 60, pp. 495-497 (1995).
Hess, Samuel T., et al., "Ultra-High Resolution Imaging by Fluorescence Photoactivation Localization Microscopy," *Biophysical Journal*, vol. 91, pp. 4258-4272 (Dec. 2006).
Hilton, Diana, "ICMOS: Intensified CMOS Camera for Biological Application," *Instrument Development for Biological Research (IDBR), Proposal to NSF*, 9 pgs. (2006).
Holden, Seamus J., et al., "DAOSTORM: an algorithm for high-density super-resolution microscopy," *Nature Methods*, vol. 8, No. 4, pp. 279-280 (Apr. 2011).
Huang, Fang, et al., "Video-rate nanoscopy enabled by sCMOS camera-specific single-molecule localization algorithms," *Nat Methods*, 10(7), 18 pgs. (Jul. 2013).
Lemmer, P., et al., "SPDM: light microscopy with single-molecule resolution at the nanoscale," *Appl. Phys. B.*, 12 pgs. (Jun. 8, 2008).
Niclass, Cristiano, et al., "A 128×128 Single-Photon Image Sensor With Column-Level 10-Bit Time-to-Digital Converter Array," *IEEE Journal of Solid-State Circuits*, vol. 43, No. 12, pp. 2977-2989 (Dec. 2008).
Ohnuki, Tohru, et al., "Development of an Ultra-fast Single-Photon Counting Imager for Single-Molecule Imaging," *Proc. of SPIE*, vol. 6092, 9 pgs. (2006).
Rust, Michael J., et al., "Sub-diffraction-limit imaging by stochastic optical reconstruction microscope (STORM)," *Nature Methods*, 3 pgs. (Aug. 9, 2006).
Shroff, Hari, et al., "Dual-color superresolution imaging of genetically expressed probes within individual adhesion complexes," *PNAS*, vol. 104, No. 1, pp. 20308-20313 (Dec. 18, 2007).
Shroff, Hari, et al., "Live-cell photoactivated localization microscopy of nanoscale adhesion dynamics," *Nature Methods*, vol. 5, No. 5, pp. 417-423 (May 2008).
Wäldchen, Sina, et al., "Light-induced cell damage in live-cell super-Resolution microscopy," *Scientific Reports*, vol. 5, 12 pgs. (2015).
"Intensified Fast CMOS Camera" of GiGE Vision http://alliedscientificpro.com/shop/intensified-fast-cmos-camera/.
"UltraCam7" of Videoscope International Ltd., Dulles, USA.
"i-Phantom: Imagine Intensified Phantom High Speed Digital Camera" of Seika Corporation (2004).
Brochure, HiCATT, High-Speed Camera Attachment; http://samwoosc.co.kr/high_speed_camera/hicatt,%20high%20speed%20camera%20attachment/html, date unknown, 1 page.

* cited by examiner

FAST HIGH-RESOLUTION MICROSCOPY METHOD AND FAST HIGH-RESOLUTION MICROSCOPE

PRIORITY CLAIM

The present application claims priority to German Patent Application No. 102015121920.4, filed on Dec. 16, 2015, which said application is incorporated by reference in its entirety herein.

FIELD OF THE INVENTION

The invention relates to a method for high-speed high-resolution localization microscopy of a specimen containing fluorescence emitters in which the fluorescence emitters in the specimen are excited to emit fluorescent radiation and the specimen is imaged in the widefield with a spatial resolution, the excitation is effected such that at least some fluorescence emitters are isolated in terms of spatial resolution, and in a localization analysis locations are determined for the isolated fluorescence emitters with an accuracy which exceeds the spatial resolution.

The invention further relates to a high-resolution microscope for high-speed localization microscopy of a specimen containing fluorescence emitters that comprises an excitation device, which is designed to excite the fluorescence emitters in the specimen to emit fluorescent radiation, and an imaging device that is designed to image the specimen with a spatial resolution, wherein the excitation device is designed in such a way that at least some fluorescence emitters are isolated in the image in terms of spatial resolution, and the microscope comprises a localization analysis device that is designed to determine a location for the isolated fluorescence emitters with an accuracy which exceeds the spatial resolution.

BACKGROUND OF THE INVENTION

In the state of the art, different methods have been developed in microscopy to break the diffraction barrier. From WO 2006/127692 or DE 102006021317 A1, a method abbreviated to PALM (photoactivated localization microscopy) is known that uses a label substance for imaging a specimen, which label can be activated e.g. by means of optical radiation. Only in the activated state the label substance can emit particular fluorescent radiation. Non-activated label molecules do not emit any, or at least no noticeable fluorescent radiation, even after irradiation with excitation radiation. The activation radiation is therefore generally referred to as switchover signal and the molecules as photoswitches. In PALM, the switchover signal is applied in such a way that at least some activated labels are spaced apart from neighboring activated labels in such a way that—in terms of the optical resolution of the microscopy—these labels are separated or can be subsequently separated by image processing methods. It is said that a subset of the fluorescence emitters is isolated. An individual image is captured for the specimen prepared in this way. Therein, the center of the radiation distribution, which is caused by resolution limitation, of the isolated emitters is determined. The position of the molecules can be calculated therefrom with a higher degree of accuracy than is actually allowed by the optical resolution. This procedure is referred to as localization. The increased resolution is also referred to as "super resolution". It requires that, in the specimen at least a subset of the activated labels can be distinguished, that is isolated within the given optical resolution. Then their location can be determined with greater accuracy; they can be localized.

The PALM method utilizes statistical effects to isolate individual label molecules. By setting the intensity of the switchover signal, it can be ensured that the probability of a label present in a given area of the specimen being activated is so low that there are sufficient sub-areas in which only labels can emit fluorescent radiation which can be distinguished within the optical resolution of the microscope. The sequence of isolation and localization is repeated several times, wherein each time a differently composed subset contributes to an individual image. The localization data from these individual images are finally compiled to form a high-resolving overall image.

The PALM method was refined, e.g., in DE 102008024568 A1 with respect to the activation of the labels to be detected. For this, fluorescent labels are used that have particular electronic states. They are activated by illumination radiation of high intensity in such a way that the great majority of the molecules are brought into an electronic, not fluorescent dark state. The remaining, then fluorescing molecules, can thus be isolated with respect to the optical resolution. The imaging and capture of the individual images is done as soon as a sufficient proportion of the molecules has been brought into the dark state, i.e. synchronized with the excitation. The exposure time for an individual image is based on the average time it takes to bring a label to the dark state by constant irradiation of excitation radiation. DE 102008024568 A1 requires a manipulation of the molecules in the specimen to the effect that the lifetime of the dark state is extended through the addition of chemical substances.

It is also noted that, in the meantime, modifications of PALM have been described in the technical literature which have received other abbreviations, such as for example STORM, dSTORM etc. Therefore, this description uses the term "localization microscopy" to cover all microscopy methods which achieve a spatial resolution beyond the optical resolution of the apparatus used by first isolating and then localizing fluorescent molecules.

As a rule, localization microscopy does not require a high spatial resolution for the illumination. A simple widefield illumination suffices in many cases. However, it requires many individual images of the specimen to be captured which in each case contain isolated molecules. In order to image the specimen completely, the total of all of the individual images must ensure that, as far as possible, all of the molecules were isolated in at least one individual image. For localization microscopy, the mentioned plurality of individual images must therefore routinely be captured, which involves a certain duration to generate an overall image.

Capturing time is also a problem for localization microscopy in that widefield detection, which is advantageous in and of itself, necessarily also requires a two-dimensional detector which must be sufficient sensitive to the detection of individual molecules. The sensitivity, usually indicated by the quantum efficiency, and the readout noise must be such that ideally individual, isolated molecules can be detected. This requirement sets for the cameras used in the state of the art in localization microscopy, a lower limit for the integration time in the capture of an individual image and thus an upper limit for the image refresh rate.

Time restraints are of particular concern when live-cell microscopy is to be carried out. In order to bring localization microscopy into a suitable time regime for this, it could be considered to take several molecules into evaluation for each diffraction-limited spot, therefore to broaden the term "isolated" to the effect that it is sufficient to isolate a group of molecules from neighboring molecule groups in terms of the resolution limit of the imaging, which limit is a diffraction-limited spot. Then, the density of the activated molecules could already be increased during the data capture and a given number of molecules could be detected more rapidly. However, in the case of current microscopy methods, this would be too much at the expense of localization accuracy.

DE 102008024568 A1 attempts to avoid the problem of the integration duration in that the lifetime of the dark state is increased by a chemical manipulation. A similar approach is taken by Heilemann et al., "Super-resolution imaging with small organic fluorophores.", *Angewandte Chemie International Edition*, 48.37, (2009): 6903-6908. Here, the integration time can be set appropriately for the separation of individual molecule occurrences. However, the specimen then needs to be chemically manipulated.

So-called fluctuation analysis, which is also called SOFI, represents another route to high resolution. Here, individual fluorophores are caused to blink, and the blinking specimen is imaged in a widefield detection. The increase in resolution then takes place not through localization but through a correlation between the different blinking states. The approach of SOFI microscopy can be seen in analogy with recognition of a light-house in shipping. There, a particular light-house will differ from other light-houses in its blinking behavior. When, at one and the same location, blinking occurs which differs from the blinking of neighboring points, it is clear that there must be an emitter (light-house in shipping—fluorescent molecule in microscopy) at this location. SOFI microscopy requires that the correlated fluctuations must occur in a timescale that is accessible to the camera. This, finally, requires quite particular dyes or labels, e.g. so-called quantum dots, that blink slowly enough. These dyes are not very to not at all suitable for living specimens. In addition, here too there is the problem of a long measurement length since a certain minimum number of individual images are required for a relevant increase in resolution. As in DE 102008024568 A1, the integration period of the camera is also adapted to the duration of the bright state of the blinking emitters. Since SOFI microscopy evaluates correlations and operates without the steps of isolation and of localization, it does not count as localization microscopy. In addition, the possible increase in resolution is limited compared with localization microscopy. A further aspect in the case of live-cell microscopy is light damage; Waeldchen et al., Scientific Reports, 5:15348, DOI: 10.1038/srep15348, October 2015, show that irradiation with short wavelengths is many times more damaging than with longer-wave light. The switching wavelength used for PALM/dSTORM etc. is 405 nm, a further reason to dispense with photoswitches.

SUMMARY OF THE INVENTION

There is therefore a need for a high-resolution microscopy method which is not limited with respect to the choice of fluorescence emitters and, in particular, does not require any chemical manipulation of fluorescence emitters. In particular, high-speed microscopy is desired. Such a method is demanded in particular for live-cell microscopy.

It is an object of the present invention to specify a localization microscopy method and to provide a microscope designed for this with which conventional dyes enable a high-speed imaging without chemical manipulation.

The invention provides for a high-speed high-resolution microscopy method of a specimen containing fluorescence emitters. Fluorescence emitters are used that have a first and a second state. The first state is a bright state in which the fluorescence emitters emit fluorescent radiation on irradiation of excitation radiation. The second state is a dark state in which the fluorescence emitters do not emit fluorescent radiation on irradiation of excitation radiation. The fluorescence emitters can be brought from the bright state into the dark state by irradiation of excitation radiation. The dark state has a particular lifetime after which the fluorescence emitters return to the bright state by themselves. The specimen and thus the fluorescence emitters is/are illuminated in the widefield with excitation radiation of an intensity. The fluorescence emitters are thereby excited to blink, in which they switch back and forth between a natural, i.e. chemically unmodified bright and dark state at a blinking frequency. The blinking specimen is imaged in widefield with a spatial resolution and is detected with a camera. The intensity of the excitation radiation is set such that at least some fluorescence emitters are isolated based on the spatial resolution in the individual images. The intensity of the excitation radiation and a refresh rate of the camera are adapted to each other such that the refresh rate with which the individual images are produced is not lower than the average blinking frequency. The individual images are subjected to a localization analysis, wherein locations are determined for isolated fluorescence emitters in the individual images with an accuracy that exceeds the spatial resolution.

The present invention further provides a high-resolution microscope for fast microscopy of a specimen containing fluorescence emitters. The microscope comprises an excitation device which is designed to irradiate the specimen in the widefield with excitation radiation to emit fluorescent radiation. The microscope further comprises an imaging device that is designed to image the specimen in the widefield with a spatial resolution. The excitation device is designed such that at least some fluorescence emitters are isolated in the imaging based on the spatial resolution. A localization analysis device is designed to determine locations for the isolated fluorescence emitters with an accuracy that exceeds the spatial resolution. A control device is designed to control the excitation device and the imaging device in accordance with the mentioned microscopy method. The localization analysis device and the control analysis device can be combined into one device.

The present invention uses fluorescence emitters for localization microscopy that can be excited by illumination with excitation radiation, i.e. light of a particular wavelength, to emit fluorescent radiation and then emit fluorescent radiation on excitation. Under illumination with excitation radiation the fluorescence emitters constantly pass through a cycle between a non-excited ground state and an excited state and back again into the ground state. The transformation from the ground state into the excited state is stimulated by the excitation radiation. On a molecular level, this is explained by the absorption of a photon of the excitation radiation. From the excited state, the fluorescence emitter returns to the ground state and emits optical fluorescent radiation during that return. On a molecular level, this change from the excited state into the ground state is connected with the emission of a fluorescence photon. The period that the fluorescence emitter remains in the excited state is in the nanosecond scale, i.e. after absorption of an excitation photon, the fluorescence emitter remains in the excited state as good as not at all, but rather emits the fluorescence photon more or less immediately. The consequence of this situation is that a fluorescence emitter that is illuminated with excitation radiation emits fluorescent radiation continuously.

This state of the fluorescence emitter, in which it can be excited at any time with excitation radiation and emits fluorescent radiation as long as it is illuminated is referred to in this description as "bright state". Contrasted with this is a dark state in which the fluorescence emitter does not emit any fluorescent radiation in spite of irradiation of excitation radiation, therefore is almost insensitive to excitation radiation. This dark state can be, for example, a so-called triplet state of the molecule. Such dark states and in particular triplet states have a certain lifetime, i.e. it takes a certain time for a fluorescence emitter to return (without emission of optical radiation) from the dark state into the ground state and thus to be in the bright state, since from the ground state in turn an excitation with excitation radiation and emission of fluorescent radiation is possible at any time. The lifetime of the dark state is significantly longer than the lifetime of the excited state. In other words, within the framework of this invention, the bright state comprises the ground state and the excited state of a fluorescence emitter from which fluorescent radiation is emitted. In contrast, the dark state is a state in which it is not possible to bring the fluorescence emitter to the excited state and thus no fluorescent radiation is emitted, even under illumination of excitation radiation.

On irradiation of excitation radiation, the fluorescence emitters remain in the bright state at a first probability. At a second probability, which is smaller than the first probability, they pass into the dark state. Since, however, the lifetime of the dark state is much longer than the lifetime of the excited state the probability that a fluorescence emitter will transfer to the dark state within a particular period of time increases with increasing intensity of the excitation radiation. An emitter remains in the dark state for the lifetime thereof and is therefore almost switched off for this lifetime since it is insensitive to excitation radiation then. Unlike the dark state, no unambiguous lifetime can be attributed to the bright state itself. A lifetime can only be attributed to the excited state of the bright state. As already stated, this is many times shorter than the lifetime of the dark state, however. In a theoretical 2-state system, a fluorescence emitter excited with excitation radiation of a particular intensity could emit fluorescent radiation almost unlimited.

The present invention uses the generic property of almost all fluorescence emitters that, on irradiation of excitation radiation, a particular proportion of the fluorescence emitters transfers to the dark state, for example to the triplet state. The proportion of the fluorescence emitters which comes into the dark state depends on the intensity of the excitation radiation. It increases as the excitation radiation intensity increases. For each fluorescence emitter there is a certain probability that it will pass from the ground state into the normal excited state through an excitation photon and from there, radiationless, into the dark state. The term "radiationless" relates to the wavelength of the fluorescent radiation. As a rule, the probability to be in the dark state increases as the intensity of the excitation radiation increases. If a fluorescence emitter is in the dark state it does not emit any fluorescent radiation for the lifetime of the dark state. Only when it had returned from the dark state into the bright state, an emitter can emit fluorescent radiation again, given that it is excited. Due to these circumstances, the fluorescence emitter blinks, the dark time of which is determined by the lifetime of the dark state. Since the emitter is luminating while in the bright state and excited, the length of the bright time depends on how long it takes for the fluorescence emitter to pass from the bright state into the dark state—ultimately the average bright time depends on the intensity of the excitation radiation. The period, and thus the blinking frequency of the blinking, is formed by the sum of the bright time and the average lifetime of the dark state. As the duration of the dark time depends on the excitation intensity, the blinking frequency is set by the choice of the excitation intensity.

In some embodiments the dark time, i.e. the average lifetime of the dark state, is predetermined molecule-specifically for all blinking frequencies. In some embodiments it is not chemically manipulated, i.e. the dark time is the lifetime of the natural dark state. In other words, the blinking is produced in that the continuous luminating of each fluorescence emitter in the bright state is interrupted by a temporary change of the fluorescence emitter into the dark state through a suitable choice of the intensity of the excitation radiation.

The present invention makes dyes blink at a desired frequency by suitable choice of the excitation intensity, performs localization microscopy and gears the integration time or image frequency of the camera to the blinking frequency. For several reasons, this represents a systematic shift away from the state of the art:

1. The invention deliberately brings about blinking of the fluorescence emitters and uses this blinking for the localization microscopy. The image capture is designed such that the refresh rate is not lower than the blinking frequency. For the localization microscopy, a fluorescence emitter is necessarily detected several times since it is blinking. In contrast, conventional PALM approaches and modifications thereof aim to bring a molecule into an illuminated state only once if possible and precisely avoid blinking at any rate.

2. For conventional fluorophores and thus for the vast majority of usual applications of fluorescence microscopy, the probability of transition into the dark state is, as mentioned, dependent on the intensity of the excitation radiation; the bright time and thus the blinking frequency change inversely with respect to each other. The more intensive the excitation radiation is, the more fluorophores pass into the dark state and the shorter the bright time (higher the blinking frequency) is. The blinking frequency can therefore be set appropriately with simple optical means and adapted to the need of the camera. By increasing the blinking frequency, the period that a molecule is in the bright state decreases. Although the dark state remains unchanged in length since it is preferably the natural dark state that has a fixed molecule-specific lifetime. The ratio between bright time and dark time is thus controlled in that the dark state becomes longer relative to the bright time. On a relative scale, a result is thus achieved that was only possible in the state of the art with chemical manipulation, i.e. extension of the dark state.

3. By referring to the blinking frequency, the present invention achieves an advantageous utilization of the interaction of integration time/image frequency of the camera and intensity of the excitation radiation, with the result that conventional fluorophores, which had been not available in PALM, can be used for localization microscopy without chemical influence.

4. A refresh rate of the camera that is not lower than the blinking frequency can be obtained through suitable, mutual adaptation of the intensity of the excitation radiation of the setting of the camera, for example of an integration time of image capture. An inverse relationship between blinking frequency defined by excitation radiation intensity and detection sensitivity of the camera defined by camera integration time/refresh rate is thus utilized. Some embodiments utilize a multi-emitter analysis in the localization analysis, i.e. understand the term "isolated", or the definition that at least some fluorescence emitters are isolated in view of the spatial resolution in the individual images, to the effect that groups of fluorescence emitters are isolated from other groups of fluorescence emitters. Since the camera nevertheless operates in a favorable performance range, the resolution is not reduced as greatly as to be expected in the state of the art.

5. Reference to the blinking frequency ensures that precisely one dark state of a blinking molecule is contained in every individual image since the refresh rate of the individual images is not lower than the blinking frequency. This frequency is composed from one bright state and one dark state. The localization of the corresponding molecule is thus still possible with conventional methods. The localization analysis of the microscopy method according to the present invention does not fundamentally differ therefore from that of standard PALM or modifications thereof. However, since the fluorescence emitters of the specimen emit several photons during their bright time, each molecule is now detected by several photons. This provides an advantageous compensation for the integration time which is comparatively short compared with the state of the art and is adapted to the blinking frequency. The relatively rapid image capture surprisingly does not lead to a poorer signal/noise ratio in the localization analysis.

In order to adapt the intensity of the excitation radiation and the refresh rate to each other, some embodiments of the present invention measure the lifetime of the dark state in a test measurement and set the refresh rate correspondingly. To measure the lifetime, the excitation radiation can be radiated in in a pulsed manner and the fluorescent radiation can be detected synchronized thereto. It is also possible to excite in continuous-wave operation and to perform an autocorrelation analysis, as it is known, e.g. from fluorescence correlation spectroscopy.

The integration time is preferably 90 percent, particularly preferably 50 percent and quite particularly preferably 10 percent of the lifetime of the dark state.

The invention operates in a time regime of the order of magnitude of the dark lifetime of most standard fluorophores. This range lies between 1 and 300 µs. The excitation intensity is set such that the blinking behavior is dominated by the lifetime of the non-fluorescing dark state. In most cases this is a triplet state. It is preferred to set the intensity of the excitation radiation such that the image frequency does not fall below a value of $1/(300\ \mu s)$.

In an embodiment of the microscopy method, the intensity of the excitation radiation does not exceed a value of 1 $MW/cm^2$, preferably of 50 $kW/cm^2$, particularly preferably of 2 $kW/cm^2$.

The refresh rate is preferably chosen such that it is not above 150%, further preferably 130%, particularly preferably 110% and quite particularly preferably 105%, and above 100% of the blinking frequency, wherein 100% is not reached.

In particularly preferred embodiments the fluorescence emitters are in a chemically unaffected state with respect to the lifetime of their dark state. This is of particular advantage in live-cell microscopy since a chemical effect on living cells is generally very disadvantageous. The present invention adapts the power of the excitation radiation to the refresh rate. This is advantageous in particular for live-cell microscopy since the photon stress of the specimen is reduced at quicker refresh rates.

The microscopic setup corresponds to that of a typical widefield fluorescence microscope, with the control device now adapted to control the excitation device and the imaging device to adjust the excitation intensity and refresh rate to each other. The excitation radiation can illuminate the specimen in form of continuous radiation (CW radiation). For fluorescence measurements, a pulsed excitation and an operation of the camera synchronized thereto is preferred. This synchronized operation can also be used in order to improve a ratio of signal to background radiation for emitters of individual molecules, namely when a background autofluorescence of a considerably different lifetime of the dark state and/or of the bright state, for example with a considerably longer or considerably shorter lifetime, is present in the specimen.

The invention aligns the refresh rate of the camera and the blinking frequency of the specimen to each other. There are certain advantages in setting the blinking frequency and thus the refresh rate relatively high. Then, the integration time of the camera is comparatively short. Some embodiments using a high refresh rate to utilize a SPAD detector array in the camera. It is therefore preferred for the camera to comprise a SPAD array.

SPAD arrays with large numbers of pixels are comparatively difficult to obtain and costly. In preferred embodiments, a SPAD array is used having a number of pixels of which does not yet permit a diffraction-limited imaging in the widefield. These embodiments may use the technique known from DE 102012205032 A1 of Carl Zeiss Microscopy GmbH, according to which the specimen is imaged in an image field and the position of the image field is displaced several times over the specimen. A partial individual image is obtained for each position of the image field and the obtained partial individual images are assembled to form an individual image.

Where method steps are explained below, they can be realized by a corresponding operation of a microscope that has a suitably designed control device. Where, therefore, method features are described, these relate to the design of a control device, for example through a suitable operating program. The reverse also applies of course that features of a control device that are achieved for example through corresponding programming means are intended to relate to and disclose method features of a corresponding operating method in the same way.

It is understood that the features named above and those yet to be explained below can be used not only in the stated combinations but also in other combinations or alone without departing from the spirit and scope of the present invention.

BRIEF DESCRIPTION OF THE DRAWINGS

The invention is explained in yet more detail below by way of example with reference to the attached drawings, which also disclose features essential to the invention. Localization microscopy is explained on the example of a variant of PALM. However, as explained above, this is not limiting for the invention. There are shown in.

DETAILED DESCRIPTION

Figure 1:
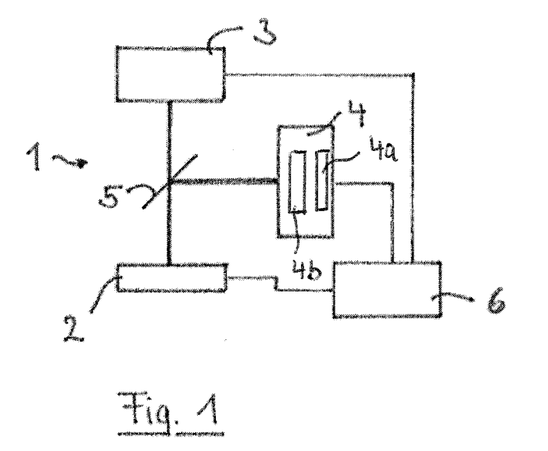
FIG. 1 a schematic representation of a microscope according to an embodiment of the invention which is based on the PALM method, FIG. 2 a flow chart for producing high-resolution images with the microscope of FIG. 1 based on the PALM method, FIG. 3 a schematic representation of a term diagram for explaining the bright and the dark state of a fluorescence emitter, FIG. 4 a timing diagram for explaining the blinking state of a fluorescence emitter, FIG. 5 a top view onto an individual image that is produced, FIG. 6 a schematic representation of a microscope for performing a high-resolution microscopy method, FIG. 7 a top view onto a surface of a specimen with different positions of an image field of the microscope of FIG. 1

FIG. 1 shows a microscope 1 schematically that images a specimen 2 in high resolution. Here, the term high resolution is used, as is usual in the state of the art, for an imaging method that has a spatial resolution that has increased beyond the diffraction limit of the imaging. The microscope 1 serves to image a specimen 2 that contains fluorescence emitters. By means of radiation from an illumination source 3, the fluorescence emitters are excited to emit fluorescent radiation. The fluorescing specimen 2 is imaged onto a widefield camera 4 via a beam splitter 5. The operation of the microscope 1 is controlled by a control device 6 that is connected to the widefield camera 4, the illumination source 3 and optionally a table on which the specimen 2 is located via corresponding control lines (not further identified) and that actuates these elements or receives data from them, in particular image data from the widefield camera 4.

In an embodiment, the widefield camera 4 comprises a combination of a CMOS camera and an image intensifier and is realized for example in the form of the "intensified fast CMOS camera" from Gige-Vision, or a CMOS camera with an upstream image intensifier, for example the image intensifier "HiCATT, high-speed camera attachment" from Lambert Instruments. In this and other embodiments, the widefield camera 4 can be adjusted with respect to its refresh rate, i.e. the exposure time or integration time. The control device 6 undertakes the corresponding setting via the control lines. Further, in preferred embodiments, the control device 6 establishes synchronization to the refresh rate.

The illumination source 3 radiates excitation radiation A to the specimen. The intensity of this radiation, either in the form of CW radiation or in the form of pulsed radiation, is set by the control device 6. Furthermore, the control device 6 optionally also performs a localization analysis in the individual images that were captured and produces the high-resolution overall image from the processed individual images.

Figure 3:
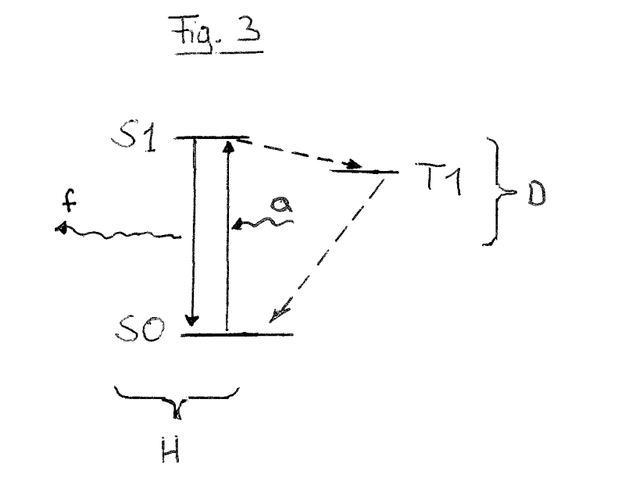

FIG. 3 shows schematically a term diagram for a fluorescence emitter that is used in the microscope 1. The fluorescence emitter has a ground state S0. Through irradiation of excitation radiation A, the fluorescence emitter passes into an excited state S1 from which it returns into the ground state with the emission of fluorescent radiation. The ground state S0 and the excited state S1 form a bright state H of the fluorescence emitter, in which it emits fluorescent radiation F at any time on irradiation of excitation radiation A. Since the lifetime of the excited state S1 is a few nanoseconds, in the bright state H a fluorescence emitter illuminated with excitation radiation A emits fluorescent radiation F continually. The fact that the emission of the individual photons of the excitation radiation F takes place at nanosecond spacing is not relevant here and could also not be detected by measurement techniques with the devices described here.

The excitation radiation A was also capable of bringing the fluorescence emitters into a triplet state T1 via the excited state S1. This has a lifetime in the range of several µs, for example between 1 and 300 µs. While the fluorescence emitter is in the triplet state T1 it does not react to further irradiation of excitation radiation A. The transitions into and out of the triplet state are radiationless (at least in relation to the wavelength of the fluorescent radiation F) and are therefore drawn with dashed lines in FIG. 3. The triplet state T1 is thus a dark state D since the fluorescence emitter then emits no fluorescent radiation F despite illumination with excitation radiation A. Only when it has returned to the ground state S0, therefore has left the dark state D and is in the bright state H again, does the fluorescence emitter emit fluorescent radiation F continually on illumination with excitation radiation A.

The probability of transition from the excited state S1 into the ground state S0 is much higher than the probability of transition from the excited state S1 into the triplet state T1. It is therefore much more probable, on irradiation of photons of the excitation radiation A, that the fluorescence emitter will remain in the bright state H than that it will change into the dark state D. However, the probability is not zero. As the intensity of the excitation radiation A increases, i.e. as it were with an increasing bombardment with photons of the excitation radiation, the probability increases that a fluorescence emitter will transfer into the dark state D within a certain period.

The term diagram shown in FIG. 3 is only to be understood as an example and is only intended to characterize the substance used here as fluorescence emitter to the effect that there is a bright state H and a dark state D which are both reached by irradiating excitation radiation A. In the dark state D, it is not absolutely necessary for a single state to be present in the form of the triplet state T1; multi-state systems are possible, too. It is important, however, that the fluorescence emitter passes into the dark state D through the incidence of the excitation radiation A with a probability of transition above zero.

This makes a substantial difference over PALM variants that use radiation of a wavelength that differs from that of the excitation radiation A. The PALM variant known as dSTORM, which operates with a specific switching radiation, is only one example. Such a separate switching radiation is not used in the embodiments of the invention. Rather, the fluorescence emitters pass into the dark state exclusively through irradiation of excitation radiation A (with a certain probability).

Figure 4:
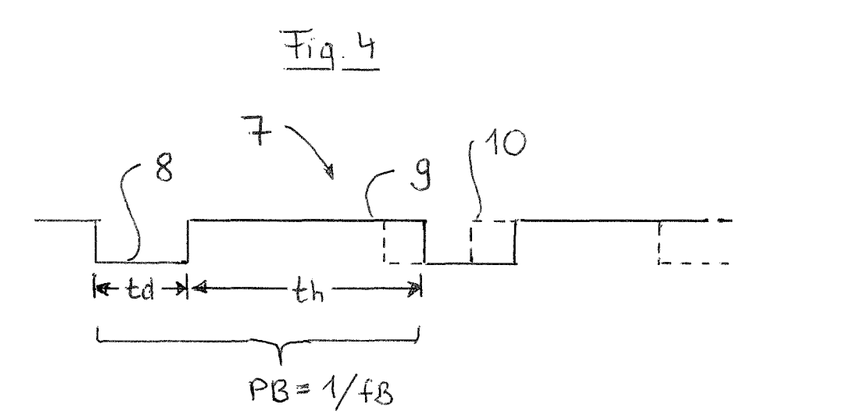

The effect of this situation is shown in FIG. 4. The figure represents the time sequence of the light emission of a fluorescence emitter, wherein a lower level 8 indicates a dark fluorescence emitter and an upper level 9 indicates a fluorescing fluorescence emitter. Through irradiation of the excitation radiation A, the fluorescence emitter passes sooner or later out of the bright state, in which it glows (upper level 9), into the dark state (lower level 8), since, as explained, it is brought into the dark state D by the excitation radiation A with a certain probability. During this dark state D, the emitter remains dark. The duration of this dark state cannot be influenced optically for the fluorescence emitter in the described case. The dark time (lower level 8 of the curve of FIG. 4) is equivalent to the lifetime td of the dark state D. Thereafter, the fluorescence emitter leaves the dark state D again and glows (upper level 9 in FIG. 4). Purely statistically, it will pass back into the dark state D again after a certain period of time. The period that it glows until then represents a bright time th. It depends on the probability of transition into the dark state D and thus on the intensity of the excitation radiation A. As a result, the fluorescence emitter performs a blinking 7, which is formed from the sequence of non-glowing (lower level 8) and glowing (upper level 9). A period PB of this blinking, the inverse of which is a blinking frequency fB, is formed by the sum of lifetime td of the dark state D and bright time th.

If the intensity of the excitation radiation A is increased, the probability increases that an emitter will pass into the dark state D, whereby the bright time th decreases. This situation is drawn in with a dashed line in FIG. 4. By increasing the intensity of the excitation radiation A, the average bright time th is shortened since the dark state D is reached earlier in the statistical average. In FIG. 4, this is plotted with a dashed line by a forwards displacement 10 of the second dark state seen from the left. It can be seen immediately that the blinking frequency fB increases (the blinking period PB decreases), wherein the lifetime td of the dark state D remains unchanged. It preferably corresponds to the natural lifetime of the dark state D, for example of the triplet state T1.

The control device 6 is designed as a whole such that the microscope 1 performs a localization-based microscopy method, for example the PALM method.

Figure 2:
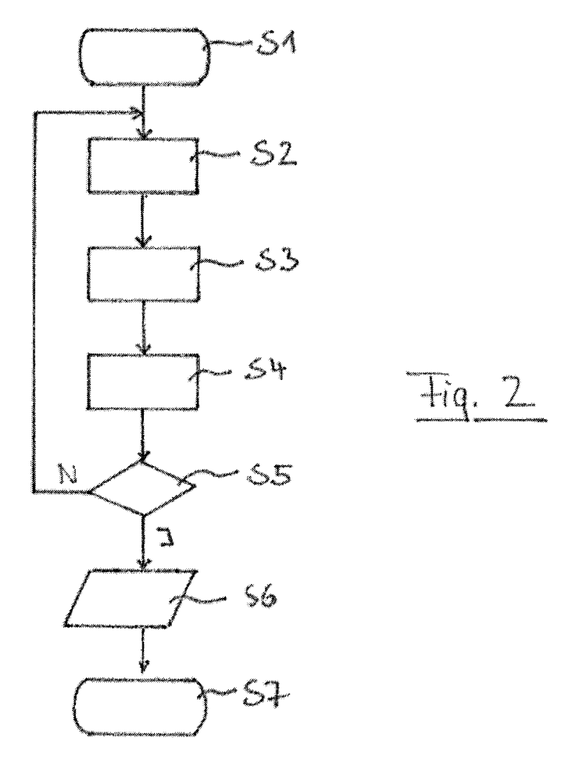

The method sequence carried out is represented in FIG. 2 as a flow diagram. After the start of the method in a step S1, in an excitation step S2 the specimen 2 is illuminated with excitation radiation A from the illumination source 3, wherein this is done in such a way that individual fluorescence emitters are isolated in terms of the spatial resolution of imaging. The imaging is done in a subsequent image capture step S3, which supplies an individual image of the specimen in widefield in that at least individual fluorescence emitters have a spacing from neighbouring fluorescence emitters that is greater than the spatial resolution of the widefield imaging. This state is shown schematically in FIG. 5, which shows an individual image 14 of the specimen 2. In the individual image, individual fluorescence emitters 11 are isolated. They are plotted as stars, here. Non-luminating fluorescence emitters, which at the present time are in a dark state D, are symbolized by rings in FIG. 5. A majority of the fluorescence emitters, in particular the fluorescence emitters in area 13, are spaced apart such that they can be separated from each other. However, individual fluorescence emitters, for example in area 12, lie so closely next to each other that they cannot be distinguished optically and in the localization analysis. The fact that 100% isolation cannot be achieved—and that this is also not at all necessary—is known to a person skilled in the art for localization analysis.

A subsequent localization step S4 determines, for these isolated fluorescence emitters, the location in the image with a spatial resolution that is greater than the diffraction limit actually allows. Fluorescence emitters, as in area 12, that cannot be separated, are discarded in the localization step S4. This can take place in that it is exploited in the localization step S4 whether the radiation captured from an isolated fluorescence emitter only originates from one or from a few fluorescence emitter(s). From this knowledge the location is determined and the fluorescence emitter is located with a greater accuracy than the diffraction limit allows. The localization analysis done in the localization step S4 can be envisaged in a simplified manner such that the center of the Airy disk of an isolated fluorescence emitter is determined, which center then represents the location. The location of the fluorescence emitter can be determined more precisely than simply determining the center by fitting a point spread function; this function can be approximated e.g. by a 2D Gaussian distribution or an experimentally determined point spread function of the optical system may be used; many different approaches are known in the state of the art, e.g. from the publications mentioned in the introductory part of the description, to perform the localization analyses.

Figure 5:
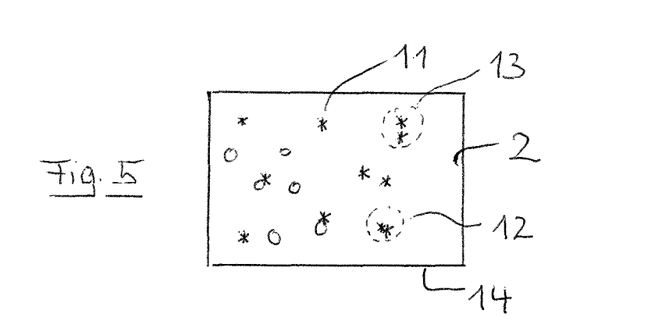

One single performance of the localization step S4 on an individual image 14 supplies a location only for those fluorescence emitters that were luminated in the corresponding widefield image, i.e. are not in the dark state D. Furthermore, only isolated fluorescence emitters are localized (therefore e.g. no emitters of area 12). In order to image the specimen with respect to, if possible, all fluorescence emitters, steps S2 to S4 are therefore repeated several times in order to have, at best, all fluorescence emitters 11 at least once in a subset of isolated fluorescence emitters. A query step S5 therefore follows the localization step S4, in which it is checked whether the specimen 2 was imaged to a sufficient extent. For example this step can access the abundance of locations that were obtained from all of the previous cycles of the localization step S4. Such a query is known to a person skilled in the art in the state of the art since such measure is also used in the PALM method or other localization-based high-resolution methods that operate without determining an error margin of location. If the specimen was detected sufficiently comprehensively (J-branch), an overall image is produced in a step S6 and the image is displayed. Otherwise (N-branch), the steps S2 to S4 are carried out again, wherein care is taken that during the repeated cycle as far as possible other fluorescence emitters are isolated.

The most advantageous (since it is the simplest) option is to first capture all of the individual images 14 and to store them and then carry out the localization analysis for each individual image 14 stored. Alternatively, in particular in case of sufficient processing capacity, an online analysis is made. After the production and display of the overall image in the image display step S6, a step S7 terminates the method. The specimen 2 was imaged with a spatial resolution which is better than the optical diffraction limit would allow.

The excitation radiation A excites the fluorescence emitters in the specimen to blink 7, in which they switch back and forth between bright state H and dark state D at a blinking frequency fB. The excitation step S2 provides the blinking specimen through suitable intensity of the excitation radiation A. The blinking specimen 2 is imaged in the image capture step S3 in a widefield imaging configuration and is detected with the widefield camera 4. The camera has a refresh rate and in consequence defines an image capture time for each individual image 14, that is determined by an integration time of the individual image production process. The control device 6 sets this integration time at the widefield camera 4. Furthermore, the control device 6 sets the intensity of the excitation radiation A at the illumination source 3.

The intensity of the excitation radiation A and the blinking frequency fB with which the fluorophores 11 blink are linked to each other. With a greatly increasing excitation intensity A, the blinking frequency fB increases. At the same time, an increasing refresh rate reduces the detection sensitivity of the widefield camera 4. A corresponding sensitivity curve or other data describing a sensitivity dependence is stored in the control device 6. Similarly, the relationship between excitation intensity A and blinking frequency fB or alternatively between excitation intensity and average bright time th is stored in the control device 6. This relationship can be stored as a curve or in the form of data (e.g. as a table). It is either known previously for the fluorophores or is determined in a special test measuring mode of the microscope, which is carried out by the control device 6 on demand or automatically. In this test measuring mode, the control device 6 detects, through synchronized, pulsed operation of illumination source 3 and widefield camera 4, the lifetime td of the dark state D and/or the bright time th and/or the blinking frequency fB—in one option as a function of the excitation intensity. Alternatively, a lifetime measurement can also take place by means of CW excitation radiation (see above).

The control device 6 sets the intensity of the excitation radiation A emitted by the illumination source 3 and the refresh rate of the widefield camera 4 in accordance with requests stored in the control device 6 or input there.

The requests can state, for example, that as quick as possible an image capture is required. The control device 6 then determines from the stored relationship between refresh rate and optical detection limit of the widefield camera 4 the minimum refresh rate that is required for imaging the specimen 2 and sets the intensity of the excitation radiation A at the illumination source 3 such that the blinking frequency fB is below the refresh rate. This operating mode can be construed as a high-speed operating mode since the reciprocal interaction of intensity of the excitation radiation A and refresh rate of the individual image capture are adapted such to minimize production of the overall image. When determining of the allowable maximum refresh rate of the individual image capture, the requirement for isolation of some of the fluorescence emitters 11 can additionally be lowered by performing the localization analyses in step S4 as multi-emitter analysis, i.e. admitting several molecules into the evaluation for each diffraction-limited spot. Thus, the performance demands on the widefield camera 4 are further reduced and the possible refresh rate increases—but this is at some but in certain applications tolerable expense of resolution.

The other extreme to as quick as possible an image capture is a reciprocal adaptation of intensity of the excitation radiation A and refresh rate in which a maximum isolation of the fluorescence emitters 11 is sought. Then, the control device 6 increases the intensity of the excitation radiation A at the illumination source 3, whereby the blinking frequency increases. At the same time, the refresh rate is also set to maximum, whereby ultimately the degree of isolation also increases. The shorter the exposure time compared with the lifetime of the dark state, the greater the isolation can become. In this way, the localization accuracy and thus the high resolution is increased—but at the expense of the photon loading or stress of the specimen.

In a preferred embodiment, the control device 6 has an input interface at which parameters with respect to the reciprocal adaptation of refresh rate and excitation radiation intensity are specified. The interface can, for example, be an input interface for a user or a data interface for supplying corresponding parameter data. In one embodiment, the parameter data or the input via a user can comprise a value that specifies an image capture rate, preferably on a relative scale, e.g. from 0 to 100. In another embodiment, alternatively or in addition, a parameter of the localization accuracy and/or the photon stress of the specimen can be specified, again preferably on a dimensionless scale. From the parameter value or the several parameter values, the control device 6 determines, in accordance with the stored relationships or tables, the refresh rate or integration time or exposure time to be set at the widefield camera 4 and the intensity of the excitation radiation A to be set at the illumination source 3 (either as CW or pulsed radiation).

As explained in the general part of the description, some embodiments comprise a control device 6 that additionally performs measurement of the characteristic variables of the emitters. This can be, for example, measurement of the blinking frequency fB or of the lifetime td of the dark state D. The microscope 1 uses a widefield camera 4 the refresh rate of which is set, or is adapted to the blinking frequency fB. In order to be able to realize high refresh rates, some embodiments use a widefield camera 4 comprising a SPAD array.

Figure 6:
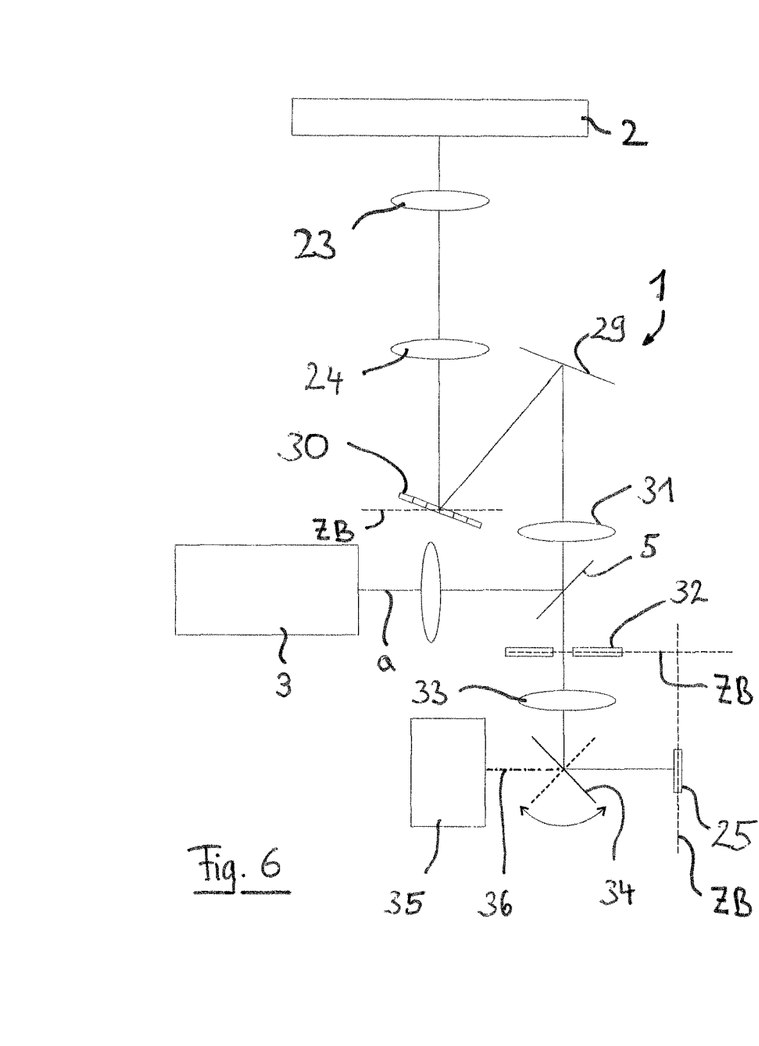

In a refinement of this approach, a SPAD array is used that theoretically would not be sufficient for the required resolution in a desired specimen field. FIG. 6 shows this embodiment of the microscope 1 schematically. The microscope 1 images the specimen 2, which is flat. A specimen area P of the specimen 2 is imaged. The microscope 1 comprises an objective 23 and a further lens 24 to image the specimen field P. Part of the specimen field P is imaged on a spatially resolving, i.e. pixelated detector 25, whereby, in contrast to the design of FIG. 1, an image field in the specimen 2 is imaged onto the detector 25, which is smaller than the specimen field to be detected. The specimen 2 is exposed to the excitation radiation A from a laser, which is one example of an illumination source 3. The excitation radiation A excites the fluorescence emitters 11 in the specimen 2 to emit fluorescent radiation F. It is coupled into the beam path to the objective 23 via an optical system that is not described in more detail and beam splitter 5. The radiation runs from beam splitter 5 to deflecting mirror 29 and adaptive mirror 30. The deflecting mirror 29 serves to keep the beam path compact and otherwise has no further importance. The adaptive mirror 30 comprises mirror segments that can be actuated individually. It is arranged in an intermediate image plane ZB of the imaging beam path and of the illumination beam path. The adaptive mirror 30 is an example of an image field shifting device for shifting the image field over the specimen area P, which image field is imaged on the detector 25. Other options are a mirror scanner or a specimen shift by specimen holder. A diaphragm 32, which is likewise arranged in an intermediate image plane ZB, also contributes to image field selection. The image of the specimen 2 reaches, via a lens 33 and a swiveling mirror 34, the detector 25, which equally lies in an intermediate image plane ZB. The swiveling mirror 34 makes it possible to view the specimen alternatively with a usual widefield camera 35. Swiveling mirror 34 and camera 35 are optional. During operation of the camera 35, the diaphragm 32 is expediently set to full open or even removed from the beam path, with the result that the whole specimen field of the specimen 2 is illuminated. In the imaging beam path, a lens 31 is also provided, which like the lens 33 also effects an intermediate imaging. Lens 31 provides for the intermediate image plane ZB, in which the diaphragm 32 is arranged; lens 33 provides for the intermediate image plane ZB, in which the detector 25 is arranged.

Figure 7:
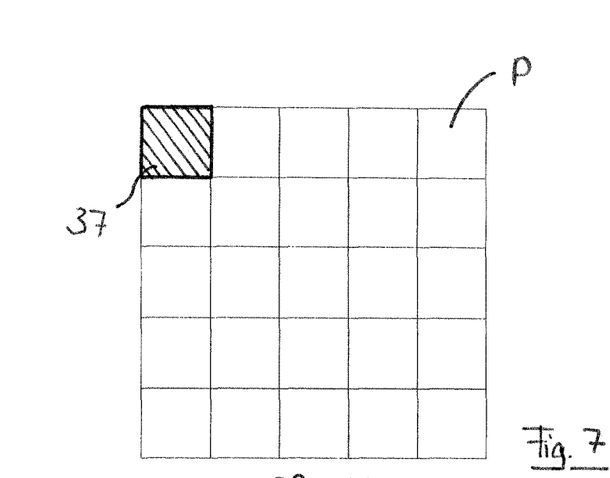

The function of the image field displacement apparatus, in the example of FIG. 6 realized by the adaptive mirror 30, is clear from FIG. 7, which shows a top view of the specimen field P of the specimen 2 to be detected. The image field, which is considerably smaller than the specimen field P, is labelled by 37. The image field 37 is shifted over the specimen field P. The corresponding shift positions and positions of the image field 37 resulting therefrom are indicated schematically in FIG. 7.

Figure 8:
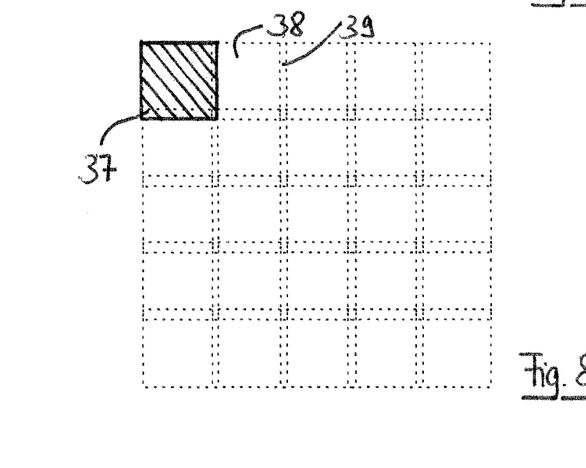
FIG. 8 a representation similar to FIG. 2 to illustrate an overlap between neighboring image field positions, FIG. 9 two fluorescence-microscopy images, wherein the upper image corresponds to a normal widefield capture and the lower image is a high-resolution overall image of the same specimen, and FIG. 10 two sectional representations through sections "1" and "2" of the images of FIG. 9.

FIG. 8 shows that the image displacement device brings the image field 37 into different positions 38 in such a way that an overlapping area 39 forms between neighboring positions 38. This is optional but makes the later assembling of individual partial images to form one image, which reproduces the specimen field P, easier.

In the embodiment with an adaptive mirror 30 the latter comprises one or more grouped elements, which shift the image field 37 over the specimen field P. The size of the image field 37 which is imaged on the detector 25 is predetermined on the one hand by the surface area of the detector 25 itself and on the other hand by the size of the diaphragm 32. This diaphragm 32 improves the imaging but is not mandatory. If it is omitted, the corresponding intermediate image plane ZB and the optical means for the production thereof can be dispensed with.

The detector 25 is a detector array with a number of pixels that would not exhaust by far the optical resolution limit, which is ultimately defined by the objective 3, if the whole specimen field P were to be imaged. The detector 25 would therefore be unsuitable per se for localization microscopy. The size of the image field 37 and the magnification ratio of the microscope 1 are therefore chosen such that a structure length in the specimen 2 corresponding to the resolution limit corresponds to the size of a pixel on the detector or is even larger. The specimen field P can nevertheless be scanned by shifting the image field 37 into several positions. Then, a detector can be used that has a high measuring speed. In the case of electronic detectors, the refresh rate of individual images is limited by the integration time and the read out time of the detector. The detector 25 of the microscope 1 can, for example, be an array of avalanche photodiodes, photomultipliers or GaAsP hybrid detectors, which have a smaller extent but are much quicker than comparatively larger conventional CMOS- or CCD-based two-dimensional detectors. The specimen field P is thus imaged on a spatially resolving detector 25, wherein the optical imaging takes place in such a way that the structure length, the maximum resolution of which is diffraction-limited, corresponds to a detector pixel in its order of magnitude on the detector. The detected image field 37 is much smaller than the specimen field P. For the detection of the whole specimen field P, the image field is brought into different positions 38. For each position, a sub-individual image 14 of the specimen 2 is captured corresponding to the current position 38. The sub-individual images are then assembled to form an individual image 14 of the specimen field P. This further development can use fast detector arrays that are available in pixel numbers which would not be enough for imaging in normal widefield. If, for example, a SPAD array with 128×128 pixels is used, as is known from the publication Niclass et al., IEEE Journal of Solid State Circuits 43, page 2977, 2008, a total of 5×5 different image field positions can cover a typical specimen field of 50 μm in size.

Figure 9:
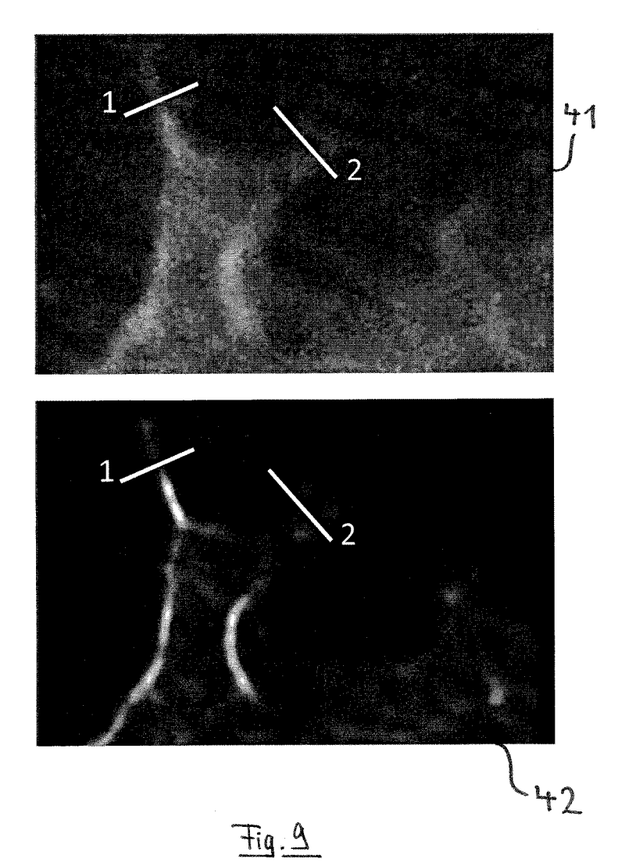

FIG. 9 shows two images that were produced with an embodiment of the described microscope. An Elyra type microscope from Carl Zeiss Microscopy GmbH was used. An Ultracam 7 from Video Scope International, Ltd., Dulles, USA was used as detector for the image capture. The fluorophores are dye Alexa 488, which marks phalloidin, which leads to parts of the cytoskeleton (actin) of the cell being stained. The intensity of the excitation radiation was 0.1 kW/cm$^2$ at a wavelength of 488 nm.

In the upper image, FIG. 9 shows a standard widefield image 41, whereas the lower image shows the high-resolution overall image 42 of the same specimen. 30,000 individual images were produced, which were captured with a frame rate of 32 kHz corresponding to an exposure time of 31.25 μs including reset time. The total measurement time took 1 s. A 2D Gaussian function was fitted for the localization analysis. Conventional PALM microscopy with an EMCCD detector would require between 10 and 17 min for the same measurement. The widefield images 41 were obtained by simply adding together the 30,000 individual frames without processing. The widefield image 41 therefore corresponds to an image with an exposure time of one second.

Figure 10:
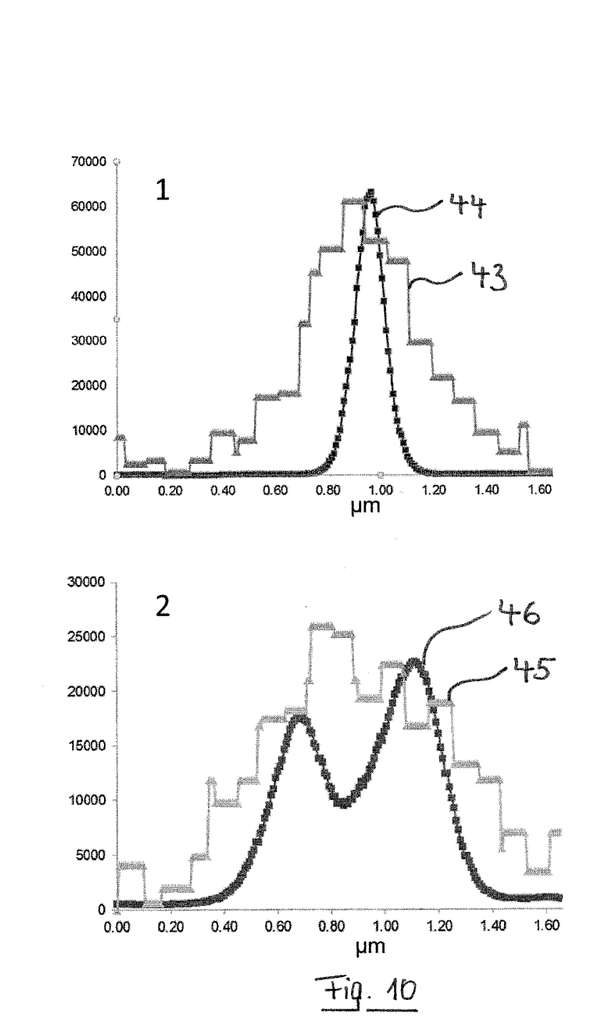

FIG. 10 shows two sections "1" and "2" that are marked in the widefield image 41 and the overall image 42 of FIG. 9. The upper representation of FIG. 10 shows two curves for the section "1", namely a curve 43 for the widefield image 41 and a curve 44 for the high-resolution overall image 42. As can be seen, the spatial resolution is very much better in the high-resolution overall image 42. The lower representation of FIG. 10 proves with reference to section "2" that incorrect information can definitely occur in the widefield for some sections, which thereby e.g. causes neighboring bright areas to overshine into the curve. This is avoided in the high-resolution overall image 42. This difference can be clearly recognized in the lower representation of FIG. 10 since the curve 45 for the widefield image 41 exhibits maxima at points at which, according to the curve 46 of the high-resolution overall image 42, there is actually no specimen structure or only a little (cf. for example in the area between 0.8 and 0.9 μm).

Where the triplet state was described previously as an example of the dark state, this is only to be understood as being by way of example. There are fluorescent dyes that are known to a person skilled in the art for fluorescence microscopy which have a dark state that is not a triplet state.

Performing the microscopy method and the corresponding design of the microscope 1 is advantageous in particular in the following time regimes: the dark lifetime td is in the range between 3 and 320 μs. The integration time of the camera is preferably shorter than this lifetime. Possible extreme values are therefore th=0.1 td, td=3 μs, PB=3.3 μs and fB=approx. 300 kHz. At another extreme, th is approximately equal to td=300 μs, PB=600 μs and fB=1.6 kHz.

The invention claimed is:

1. A fast, high-resolution microscopy method of a specimen containing a fluorescence emitter, comprising:

using in a specimen, fluorescence emitters that have a first and a second state, wherein the first state is a bright state in which the fluorescence emitters emit fluorescent radiation on irradiation of excitation radiation, and the second state is a dark state in which the fluorescence emitters do not emit fluorescent radiation on irradiation of excitation radiation, wherein the fluorescence emitters can be brought from the bright state into the dark state by irradiation of excitation radiation and the dark state has a particular lifetime after which the fluorescence emitters return to the bright state spontaneously, illuminating the specimen and the fluorescence emitters in the widefield with excitation radiation having an intensity, thereby exciting the fluorescence emitters and causing the fluorescence emitters to blink, such that the fluorescence emitters switch back and forth between a bright state and a dark state at a blinking frequency, detecting and imaging with a camera the blinking specimen in the widefield with a spatial resolution, with a camera, setting the intensity of the excitation radiation such that at least some fluorescence emitters are isolated in the individual images in terms of the spatial resolution, and the intensity of the excitation radiation and a refresh rate of the camera are adapted to each other such that the refresh rate with which the individual images are produced is not lower than the blinking frequency, and subjecting the individual images to a localization analysis, wherein locations are determined for isolated fluorescence emitters in the individual images with an accuracy that exceeds the spatial resolution.

2. The microscopy method according to claim 1, wherein an integration time for the production of an individual image is not longer than the lifetime of the dark state.

3. The microscopy method according to claim 1, wherein, in a test measurement, the excitation radiation is irradiated in a pulsed manner, the lifetime of the dark state is measured and the refresh rate is set correspondingly, with the result that an integration time is 10% of the lifetime of the dark state.

4. The microscopy method according to claim 1, wherein the integration time is not more than 300 μs.

5. The microscopy method according to claim 1, wherein the fluorescence emitters are in a chemically unaffected state with respect to the lifetime of the dark state.

6. The microscopy method according to claim 1, wherein an intensity of the excitation radiation does not exceed a value of 1 MW/cm$^2$.

7. The microscopy method according to claim 1, wherein the intensity of the excitation radiation is set such that the blinking frequency has a value of not less than 1/(300 μs).

8. The microscopy method according to claim 1, wherein in the production of the individual images the excitation radiation is irradiated as CW radiation.

9. A high-resolution microscope for fast microscopy of a specimen containing a fluorescence emitter, comprising:

an excitation device that is designed to excite the specimen in the widefield with excitation radiation to emit fluorescent radiation, an imaging device that is designed to image the specimen in the widefield with a spatial resolution, wherein the excitation device is designed such that at least some fluorescence emitters are isolated in the imaging in terms so the spatial resolution, a localization analysis device that is designed to determine locations for the isolated fluorescence emitters with an accuracy that exceeds the spatial resolution, and a control device that is designed to control the excitation apparatus and the imaging apparatus in accordance with the following method: fast high-resolution microscopy method of a specimen containing a fluorescence emitter, in which fluorescence emitters are used that have a first and a second state, wherein the first state is a bright state in which the fluorescence emitters emit fluorescent radiation on irradiation of excitation radiation, and the second state is a dark state in which the fluorescence emitters do not emit fluorescent radiation on irradiation of excitation radiation, wherein the fluorescence emitters can be brought from the bright state into the dark state by irradiation of excitation radiation and the dark state has a particular lifetime after which the fluorescence emitters return to the bright state spontaneously, the specimen and thus the fluorescence emitters are illuminated in the widefield with excitation radiation of an intensity and the fluorescence emitters are thereby excited to blink, such that they switch back and forth between bright state and dark state at a blinking frequency, the blinking specimen is imaged in the widefield with a spatial resolution and is detected with a camera, the intensity of the excitation radiation is set such that at least some fluorescence emitters are isolated in the individual images in terms of the spatial resolution, and the intensity of the excitation radiation and a refresh rate of the camera are adapted to each other such that the refresh rate with which the individual images are produced is not lower than the blinking frequency, and the individual images are subjected to a localization analysis, wherein locations are determined for isolated fluorescence emitters in the individual images with an accuracy that exceeds the spatial resolution.

10. The microscope according to claim 9, wherein the imaging device comprises a CMOS two-dimensional detector with an image intensifier connected upstream in the beam path.

11. The microscope according to claim 9, wherein the refresh rate has a value of not less than 1/(300 μs).

12. The microscope according to claim 9, wherein the imaging device comprises a SPAD array as two-dimensional detector.

13. The microscope according to claim 11, which comprises an image field displacement device in order to image a specimen field by displacing an image field onto the SPAD array and thus to assemble each individual image from several partial individual images.

14. The microscopy method according to claim 1, wherein, in a test measurement, the excitation radiation is irradiated in a pulsed manner, the lifetime of the dark state is measured and the refresh rate is set correspondingly, with the result that an integration time is 50% of the lifetime of the dark state.

15. The microscopy method according to claim 1, wherein, in a test measurement, the excitation radiation is irradiated in a pulsed manner, the lifetime of the dark state is measured and the refresh rate is set correspondingly, with the result that an integration time is 90% of the lifetime of the dark state.

16. The microscopy method according to claim 1, wherein the integration time is not more than 100/μs.

17. The microscopy method according to claim 1, wherein the integration time is not more than 50/μs.

18. The microscopy method according to claim 1, wherein the integration time is not time between 1 μs more than 30 μs.

19. The microscopy method according to claim 1, wherein an intensity of the excitation radiation does not exceed a value of 50 MW/cm$^2$.

20. The microscopy method according to claim 1, wherein an intensity of the excitation radiation does not exceed a value of 2 MW/cm$^2$.

21. The microscopy method according to claim 1, wherein the intensity of the excitation radiation is set such that the blinking frequency has a value of not less than 1/(50 μs).

22. The microscopy method according to claim 1, wherein the intensity of the excitation radiation is set such that the blinking frequency has a value of not less than 1/(1 μs).

23. The microscope according to claim 9, wherein the refresh rate has a value of not less than 1/(100 μs).

24. The microscope according to claim 9, wherein the refresh rate has a value of not less than 1/(150 μs).

25. The microscope according to claim 9, wherein the refresh rate has a value between 1/(30 μs) and 1 μs.

* * * * *

UNITED STATES PATENT AND TRADEMARK OFFICE
CERTIFICATE OF CORRECTION

PATENT NO. : 10,119,914 B2
APPLICATION NO. : 15/380880
DATED : November 6, 2018
INVENTOR(S) : Thomas Kalkbrenner Page 1 of 1

It is certified that error appears in the above-identified patent and that said Letters Patent is hereby corrected as shown below:

On the Title Page

Page 2, Column 2, Line 1, In the OTHER PUBLICATIONS, the following reference should read:
HEILEMANN, MIKE, et al., "Subdiffraction-Resolution Fluorescence Imaging with Conventional fluorescent Probes," Angew. Chem. Int. Ed., Vol. 47, pp. 6172-6176 (2008).

Page 2, Column 2, Line 34, the following reference should read:
SHROFF, HARI, et al., "Dual-color superresolution imaging of genetically expressed probes within individual adhesion complexes," PNAS, Vol. 104, No. 51, pp. 20308-20313 (December 18, 2007).

Page 2, Column 2, Line 46, the following reference should read:
"i-Phantom: Image Intensified Phantom High Speed Digital Camera" of SEIKA CORPORATION (2004).

In the Claims

At Column 18, Line 50 (Claim 16), delete "100/μs" and insert --100 μs--.

At Column 18, Line 52 (Claim 17), delete "50/μs" and insert --50 μs--.

Signed and Sealed this
Twenty-ninth Day of January, 2019

Andrei Iancu
*Director of the United States Patent and Trademark Office*